(12) United States Patent
Zhou et al.

(10) Patent No.: US 7,792,778 B2
(45) Date of Patent: Sep. 7, 2010

(54) KNOWLEDGE-BASED IMAGING CAD SYSTEM

(75) Inventors: Xiang Zhou, Exton, PA (US); Alok Gupta, Bryn Mawr, PA (US); Arun Krishnan, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 640 days.

(21) Appl. No.: 11/782,689

(22) Filed: Jul. 25, 2007

(65) Prior Publication Data

US 2008/0027889 A1 Jan. 31, 2008

Related U.S. Application Data

(60) Provisional application No. 60/834,394, filed on Jul. 31, 2006.

(51) Int. Cl.
*G06N 5/00* (2006.01)
*G06K 9/32* (2006.01)
*G06Q 50/00* (2006.01)
*G06Q 19/00* (2006.01)
*G06F 15/16* (2006.01)

(52) U.S. Cl. ............ 706/50; 382/294; 705/2; 705/3; 709/205

(58) Field of Classification Search ............ 706/13, 706/50; 705/2, 3; 382/294; 709/205
See application file for complete search history.

(56) References Cited

U.S. PATENT DOCUMENTS

| 5,608,872 A | * | 3/1997 | Schwartz et al. ............ 709/205 |
| 2003/0177038 A1 | * | 9/2003 | Rao ............... 705/2 |
| 2005/0043968 A1 | | 2/2005 | Sauerwald |

FOREIGN PATENT DOCUMENTS

WO WO 03/034274 A 4/2003

* cited by examiner

*Primary Examiner*—Donald Sparks
*Assistant Examiner*—Ola Olude Afolabi

(57) ABSTRACT

A system for knowledge-based image computer aided detection includes a text interpretation system receiving an electronic patient record and outputting an assertion relevant for the electronic patient record, an annotation/detection system detects anatomical and functional structures in input images and interacts with the text interpretation system to receive the assertion and outputting annotated images based on the input images, and an imaging decision support system taking the annotated images and outputting classifications of annotated structures in the annotated images.

12 Claims, 4 Drawing Sheets

KNOWLEDGE-BASED IMAGING CAD SYSTEM

CROSS-REFERENCE TO RELATED APPLICATION

This application claims priority to U.S. Provisional Application Ser. No. 60/834,394, filed on Jul. 31, 2006, which is herein incorporated by reference in its entirety.

BACKGROUND OF THE INVENTION

1. Technical Field

The present invention relates to computer aided detection, and more particularly to a system and method for knowledge-based image computer aided detection.

2. Discussion of Related Art

Today, all medical images are interpreted and re-coded into words (clinical reports) by human experts. Words are typically not enough, images typically include information beyond what words can describe. However, image data is unstructured and hinders automatic or efficient processing and exploitation. Doctors use whatever information is available in the EPR to guide their interpretation of the images. An imaging CAD system should do the same to improve performance.

Therefore, a need exists for an automatic EPR-guided annotation of unstructured image data (both physiologic and pathologic findings) will benefit existing domains of clinical practices that involves imaging and images.

SUMMARY OF THE INVENTION

According to an embodiment of the present disclosure, a system for knowledge-based image computer aided detection includes a text interpretation system receiving an electronic patient record and outputting an assertion relevant for the electronic patient record, an annotation/detection system detects anatomical and functional structures in input images and interacts with the text interpretation system to receive the assertion and outputting annotated images based on the input images, and an imaging decision support system taking the annotated images and outputting classifications of annotated structures in the annotated images.

According to an embodiment of the present disclosure, a system for knowledge-based image computer aided detection includes a memory device storing a plurality of instructions embodying a knowledge-based image computer aided detection system, a processor for receiving an electronic patient record and executing the plurality of instructions to perform a method including determining and outputting an assertion relevant for the electronic patient record, detecting anatomical and functional structures in an input image corresponding to the electronic patient record based on the assertion for determining an annotated image, and determining a classification of an annotated structure in the annotated image based on the assertion.

According to an embodiment of the present disclosure, a computer readable medium is provided embodying instructions executable by a processor to perform a method for knowledge-based image computer aided detection, the method including receiving an electronic patient record, determining and outputting an assertion relevant for the electronic patient record, detecting anatomical and functional structures in an input image corresponding to the electronic patient record based on the assertion for determining an annotated image, and determining a classification of an annotated structure in the annotated image based on the assertion.

BRIEF DESCRIPTION OF THE DRAWINGS

Preferred embodiments of the present invention will be described below in more detail, with reference to the accompanying drawings.

DETAILED DESCRIPTION OF EXEMPLARY EMBODIMENTS

Figure 1:
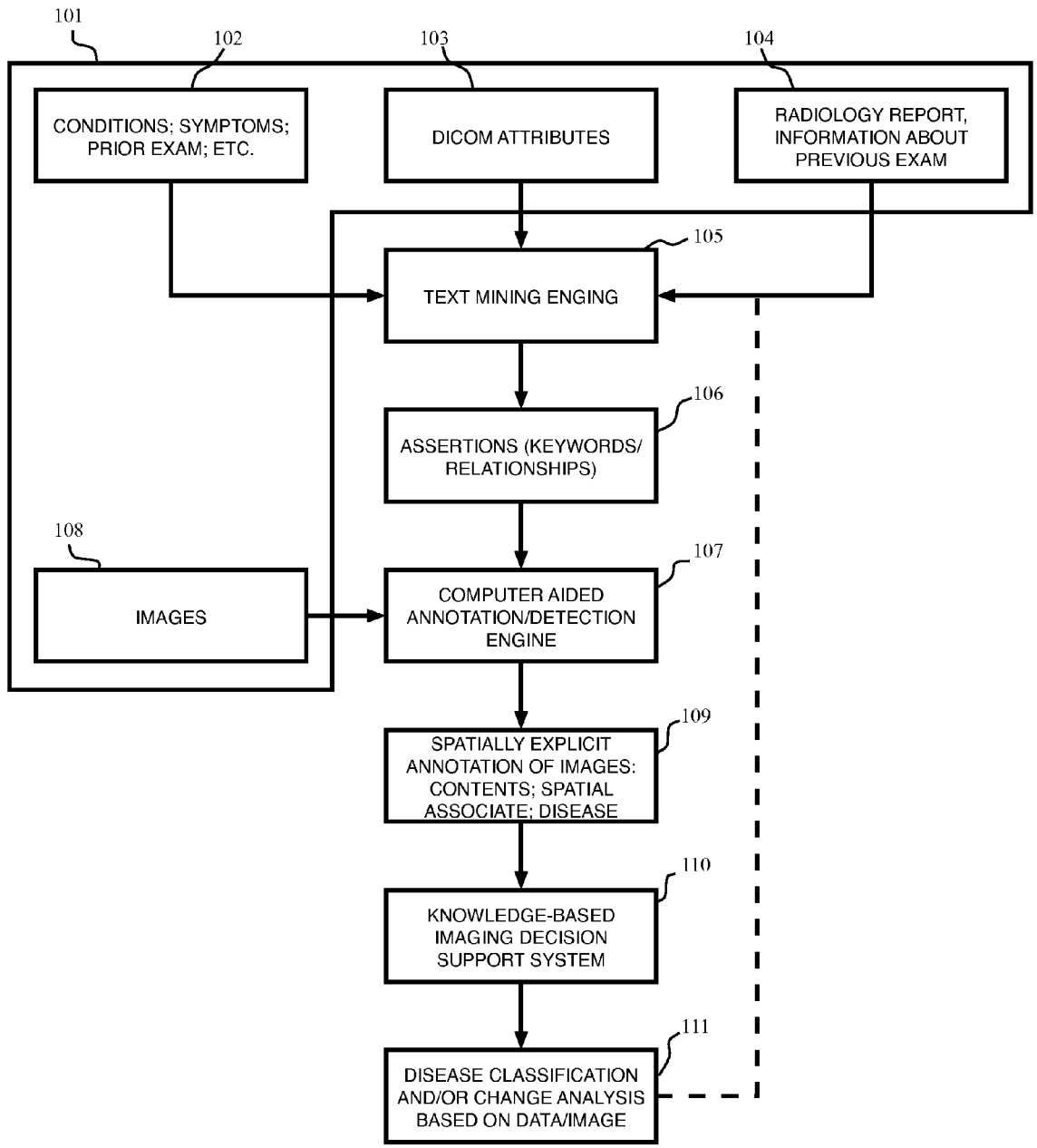
FIG. 1 is a joint image/text understanding and decision support system diagram according to an embodiment of the present disclosure.

According to an embodiment of the present disclosure,

Referring to FIG. 1, given an electronic patient record 101, a text interpretation system 105 interprets/parses the records, and outputs keywords/key phrases 106 relevant for the patient (e.g., suspected colorectal cancer). The electronic patient record 101 may include conditions 102, DICOM attributes 103, reports 104, images 108, etc.

Based on the assertions 106, in addition to, optionally, predefined keywords such as lung, breast, heart, bladder, etc., an annotation/detection system 107 detects relevant anatomical (e.g., colon in CT) or functional (e.g., tracer uptake by bladder in FDG-PET) structures in input images 108, guided by the assertions 106. The outputs are location and/or segmentation of organs and disease candidates 109.

The assertions 106 may include keywords/key-phrases, for example, "tumor" or "heart", and relationships, for example, "top", "inside", etc.

Optionally, a representation is generated of spatial and conceptual dependencies among all possible keywords, for example, using an ontology and/or graphical model, for example, a graphical model of disease/organ interactions; or an ontology of the human anatomy. With this component, the detection performance may be improved: for example, knowing the relative location of lung and bladder or heart can help the detection of these structures jointly, and help the detection of pathology of these organs as well. In addition, if the knowledge that "colorectal cancer often metastasize in liver" is coded in this representation, the system can proactively detect liver, and try to see whether there is metastasis in there.

An imaging decision support system 110 takes the annotated images and outputs classifications of the detected diseases based on the full knowledge extracted from the EPR 111. When historical data/images are available, change analysis may be performed between current and previous data/images.

Optionally, an additional inference and reasoning system for therapy selection is implemented based on the classifications or change analysis (e.g., remind).

Other possible implementations include data organization in PACS based on image and EPR contents, record linkage for searching image content to establish identity, etc.

Figure 2:
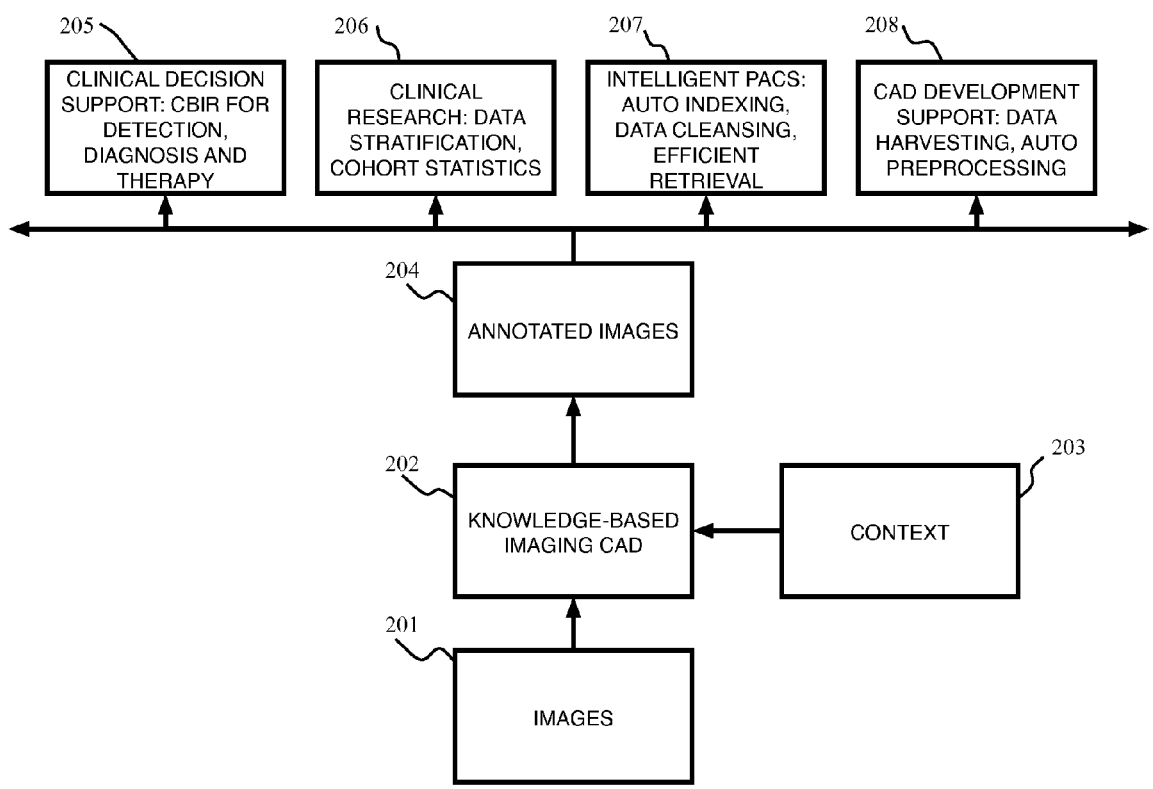
FIG. 2 is an illustration of system inputs, outputs, and application domains, according to an embodiment of the present disclosure.

Referring to FIG. 2, exemplary implementation of the present disclosure according to various embodiments will be described below.

In one exemplary implementation, a query and knowledge-based CAD 205 allows an oncologist reading a follow-up CT scan from the electronic patient records, to find out that colon polyps were found in the patient during an early scan. The system localizes the colon in the current volume, and invokes a ColonCAD tool to detect all polyps in the current scan. The system alerts the oncologist of the prior finding and flags current polyps to the oncologist 204. The oncologist may request a comparison with the previous scan. The system searches and retrieves the previous scan of the patient and a comparative analysis of the two are presented to the user with an assessment of cancerous progression of the polyps.

Based on a stored colon cancer model 203, the system knows that colorectal cancer can metastasize into liver through the bloodstream. Therefore, a knowledge-based image CAD 202 of the system automatically finds the liver in the images 201 and performs a check for potential metastatic lesions. The oncologist types in a query to find similar cases in the database with know interventional outcomes. The system searches for other colon poly patients with similar poly location and statistics and a similar rate of progression. The system summarizes the retrieval results based on interventions and outcomes and present similar patients and recommended interventional options to the oncologist.

In another exemplary implementation, for pharmaceutical applications 206, a study may have suggested that when primary lung tumor is in the left lower lobe (LLL) surgery should be considered carefully because of the significantly lower survival rate. A medical statistician working at a pharmaceutical company is looking for a cohort of lung caner patients whose cancer appears only in the LLL without metastasis for a specific drug trial. She queries Quaero-Medico and the computer automatically mines a large-scale distributed image databases candidate, computer inspects the lung as well as the other organs. For each possible only LLL tumor are present and with no lymph node involvement or metastasis. The resulting subset is presented to the user.

In an exemplary implementation for citizen applications 207 consider the case of "Jack" who is 65 years old and has a family history of heart disease. With the aging process his heart is becoming weaker. Although he has no symptoms, he has kept up regular check-up using echocardiogram, as well as cardiac CT occasionally. He brings home is echocardiogram and CT images 201. He also subscribes to a shared medical image repository through the web 203. He submits his images and requests for similar cases to be returned from his age group and with a similar family history. The system using the knowledge-based imaging CAD 202 and context 203 analyzes his heart images for possible defects or diseases; and returns similar cardiac disease case with known therapy and outcome. He does this regularly to be informed of new diagnostic or interventional options and of their potential benefits and side effects.

In an exemplary implementation for medical IT professionals 208 consider the case of a startup company that hires several IT professionals to build on top of Quaero-Medico some new CAD tools for a disease that is not yet modeled in Quaero-Medico. They utilize the query APIs to define their specific CAD routine 202, and use the image parser API to localize the ROI in images 201 for processing. They subscribe to the repository 203 to gain access to large amount of data for the training and testing of the new algorithm.

Figure 3:
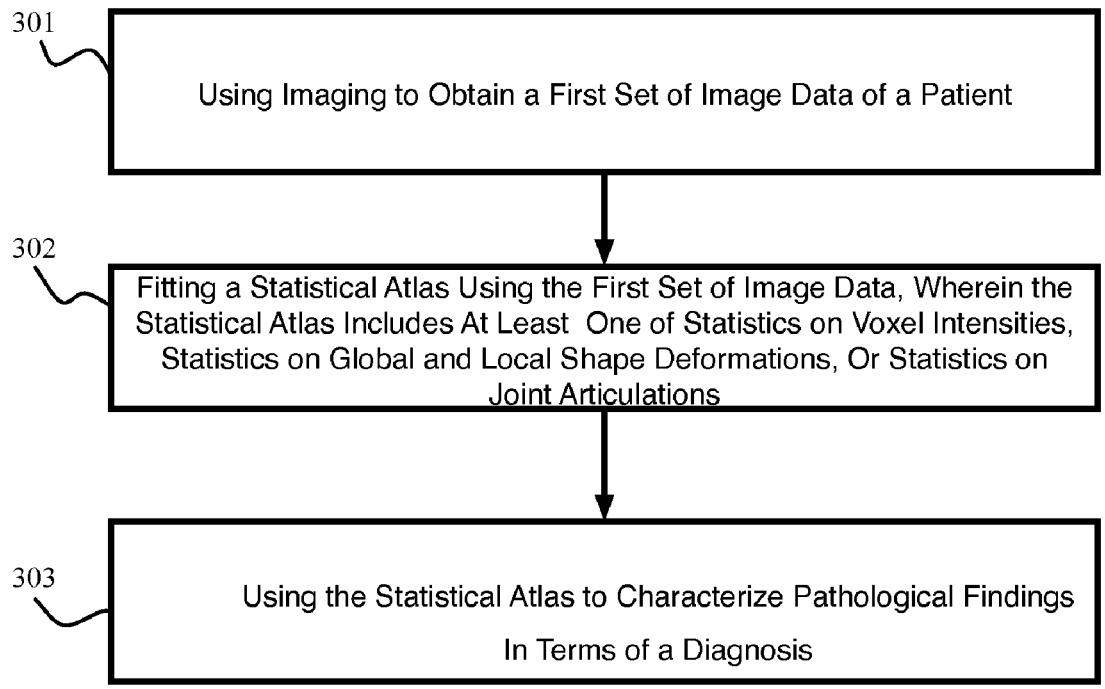
FIG. 3 is a flowchart showing a method of providing automatic diagnosis and decision support in whole-body imaging, according to an exemplary embodiment of the present invention.
Figure 4:
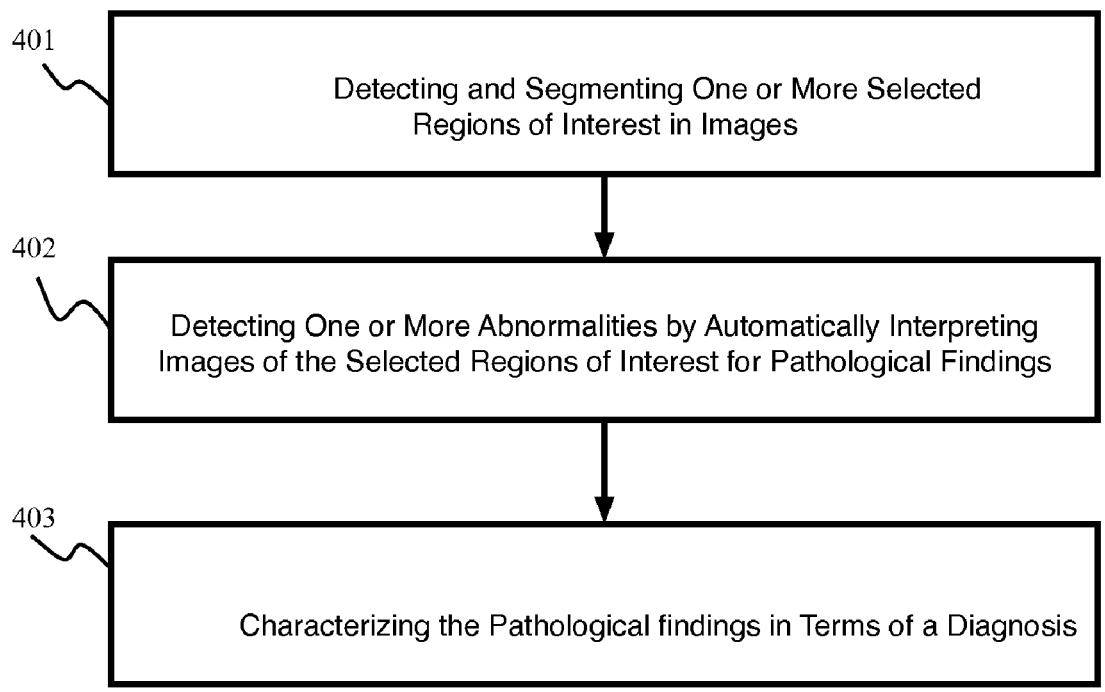
FIG. 4 is a flowchart showing a method of providing automatic diagnosis and decision support in whole-body imaging, according to an exemplary embodiment of the present invention.

In the context of the computer aided annotation/detection engine 107 and the knowledge-based imaging decision support system 110, FIGS. 3 and 4 show exemplary methods for providing automatic diagnosis and decision support in imaging. These methods take an output of the text mining engine 105, e.g., assertions about the images in the form of keywords and relationships between keywords, for improving automatic diagnosis and decision support.

FIG. 3 is a flowchart showing a method of providing automatic diagnosis and decision support in imaging, according to an exemplary embodiment of the present invention.

Referring to FIG. 3, in block 310, imaging is used to obtain a first set of image data of a patient.

The first set of image data is obtained using one or more imaging modalities. For example, the first set of image data may be obtained using whole-body positron emission tomography (PET) and one or more imaging modalities other than whole-body PET. For example, the first set of image data may be obtained using whole-body PET, CT, MRI, SPECT, PET/CT, SPECT/CT, and/or PET/MRI. The first set of image data may comprise 2-D image data, 3-D image data and/or higher-dimensional image data.

In block 320, a statistical atlas is fitted using the first set of image data. The statistical atlas may include statistics on voxel intensities, statistics on global and local shape deformations, and/or statistics on joint articulations. The statistical atlas may comprise distributional appearance models and/or spatial relational models of organs or structures in one or more whole-body imaging modalities.

In an exemplary embodiment of the present invention, the first set of image data includes PET data, and fitting the statistical atlas comprises automatically outlining selected regions of interest with pathological tracer uptakes while discounting physiological uptakes in the PET data. The first set of image data may include image data acquired by one or more imaging modalities other than PET. Using the statistical atlas to characterize pathological findings in terms of a diagnosis may comprise detecting anatomical or functional abnormalities of the whole body or body parts using the first set of image data.

Using the statistical atlas to characterize pathological findings in terms of a diagnosis may comprise automatically outlining selected regions of interest in the first set of image data and automatically extracting candidate features of interest from the selected regions of interest. Each of the candidate features of interest may be automatically contoured and characterized. For example, automatic contouring and characterizing may be based on standard uptake value and/or brain uptake normalized data.

In block 330, the statistical atlas is used to characterize pathological findings in terms of a diagnosis.

In an exemplary embodiment of the present invention, a method for providing automatic diagnosis and decision support in imaging further includes using imaging to obtain a second set of image data of the patient, using the atlas for pathological findings, and updating pathological findings based on the statistical atlas using the second set of image data. The second set of image data is obtained using one or more imaging modalities. For example, the second set of image data may be obtained using whole-body PET, CT, MRI, SPECT, PET/CT, SPECT/CT, and/or PET/MRI. Updating pathological findings based on the statistical whole-body atlas may comprise encoding anatomical or functional variations of the whole body or body parts using the second set of image data.

In an exemplary embodiment of the present invention, a method for providing automatic diagnosis and decision support in imaging further includes using imaging to obtain a third set of image data of the patient, using the whole-body atlas for pathological findings, and updating pathological findings based on the statistical atlas using the third set of image data. The third set of image data is obtained using one or more imaging modalities. For example, the third set of image data may be obtained using whole-body PET, CT, MRI, SPECT, PET/CT, SPECT/CT, and/or PET/MRI. Updating pathological findings based on the statistical atlas may comprise encoding anatomical or functional variations of the whole body or body parts using the third set of image data.

FIG. 4 is a flowchart showing a method of providing automatic diagnosis and decision support in imaging, according to an exemplary embodiment of the present invention.

Referring to FIG. 4, in block 410, one or more selected regions of interest are detected and segmented. Segmenting the selected regions of interest may be accomplished using bounding boxes, centroid locations, bounding surfaces and/or a bounding mask. Segmenting the selected regions of interest may be automatically performed.

Although not shown in FIG. 4, a method of providing automatic diagnosis and decision support in imaging in accordance with an exemplary embodiment of the present invention may include detecting hotspots in the selected regions of interest from PET or SPECT images. The hotspots may be localized based on anatomical dependencies, and may be segmented using organ-specific thresholds. For example, to detect metastatic spread in bones, one needs to see the bones first. To detect and characterize tumor involvement of lymph nodes, one may want to detect great vessels, since lymph nodes appear near these structures. CT in a PET/CT scan may be regarded as the source of anatomical context for functional hotspots revealed by PET.

In block 420, one or more abnormalities are detected by automatically interpreting images of the selected regions of interest for pathological findings. The images may be obtained using one or more imaging modalities. For example, the images may be obtained using PET, CT, MRI, SPECT, PET/CT, SPECT/CT, and/or PET/MRI. The selected regions of interest may comprise cells, tissues, organs and/or organ systems. For example, the selected regions of interest may comprise a liver, a lung or a kidney.

In block 430, the pathological findings are characterized in terms of a diagnosis. When longitudinal data is available, clinical analysis of the longitudinal data may be performed, and changes may be output in a clinically meaningful way. Since scans are often used for longitudinal studies, such as for example, oncology. Change quantification is useful during, for example, therapy response monitoring. Change quantification may be regarded as pattern detection in the context of time. Clinical priors or predispositions such as genetic predisposition are sometimes helpful for interpreting whole body images. For example, knowledge of the primary tumor location can help the assessment of regional lymph node involvement. For example, osteoarthritis will affect the PET uptake level in affected joints, menstruation cycle affects breast uptakes, and radiation therapy can result in elevated uptake levels in the axial skeleton and in neck fat.

The image understanding provided by the text mining engine 105 may further be improved by the output of the computer aided annotation/detection engine 107 and knowledge-based imaging support system 110, for example, to disambiguate text entered by a doctor, or to correct typographical errors. For example, where the same patient has two imaging scans taken over time, and the patients name is spelled different during the two scans, the system may detect a similarity between the scans, e.g., greater then 98% correlation, and link the records together, correcting the error in the input. In another example, a doctor's description of a patient having "nearly" been ride of cancer cells may be improved to give a percentage of tumor shrinkage as detected between two imaging scans.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

Figure 5:
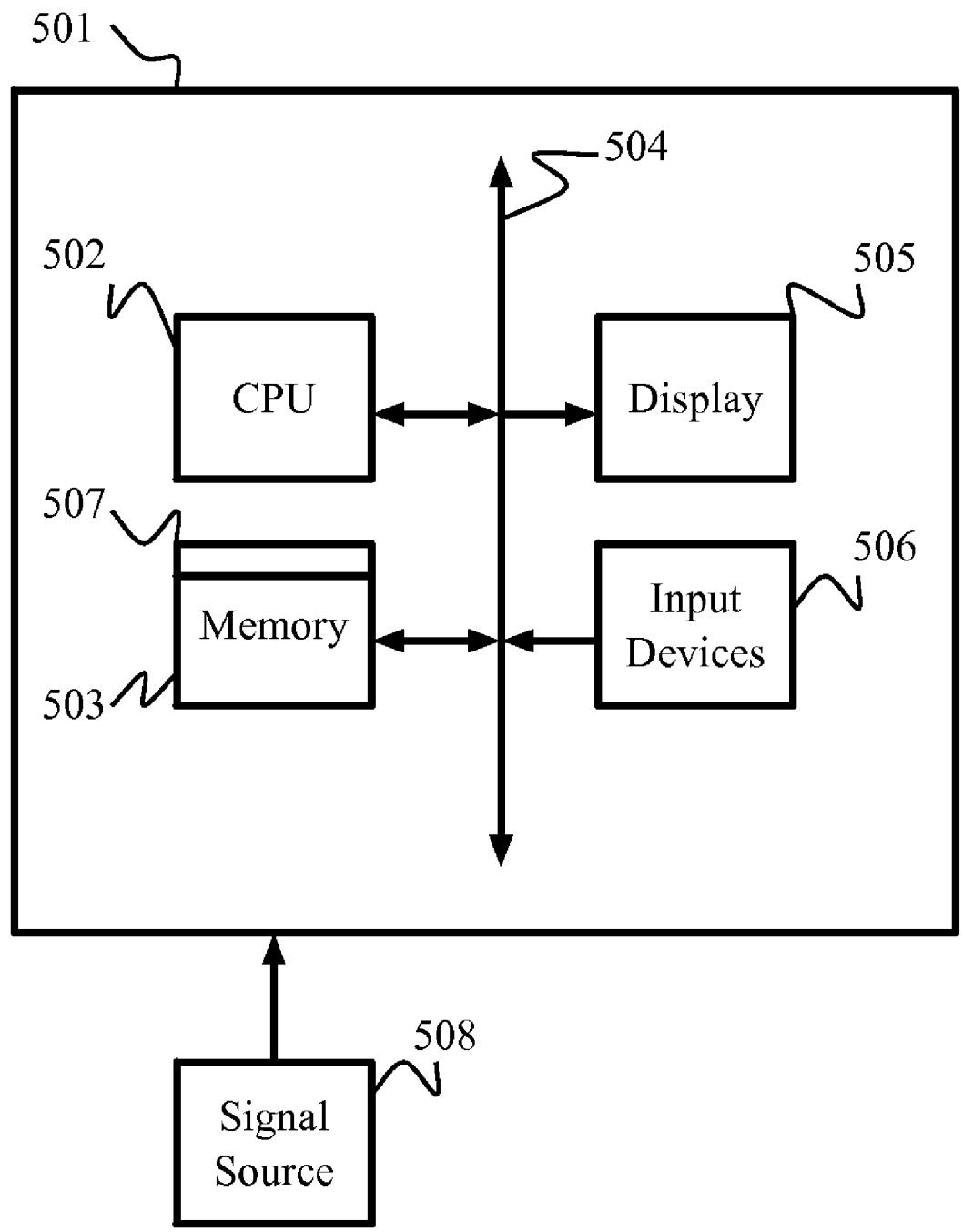
FIG. 5 is a diagram of a system according to an embodiment of the present disclosure.

Referring to FIG. 5, according to an embodiment of the present invention, a computer system 501 for knowledge-based image computer aided detection can comprise, inter alia, a central processing unit (CPU) 502, a memory 503 and an input/output (I/O) interface 504. The computer system 501 is generally coupled through the I/O interface 504 to a display 505 and various input devices 506 such as a mouse and keyboard. The support circuits can include circuits such as cache, power supplies, clock circuits, and a communications bus. The memory 503 can include random access memory (RAM), read only memory (ROM), disk drive, tape drive, etc., or a combination thereof. The present invention can be implemented as a routine 507 that is stored in memory 503 and executed by the CPU 502 to process a signal, e.g., a closed surface mesh, from the signal source 508. As such, the computer system 501 is a general purpose computer system that becomes a specific purpose computer system when executing the routine 507 of the present invention. The computer system 501 may further include a GPU 509 for processing certain operations.

The computer platform 501 also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

Having described embodiments for a system and method for knowledge-based image computer aided detection, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed is:

1. A system for knowledge-based image computer aided detection comprising:

a memory device storing a plurality of instructions embodying:
- a text interpretation system configured to receive an electronic patient record and output outputting an assertion relevant for the electronic patient record;
- an annotation/detection system configured to detect anatomical and functional structures in input images and interact with the text interpretation system to receive the assertion and output annotated images based on the input images; and
- an imaging decision support system configured to receive the annotated images and output classifications of annotated structures in the annotated images;
- wherein the annotation/detection system detects anatomical and functional structures in input images guided at least in part by the assertion; and
- a processor for receiving the electronic patient record and executing the plurality of instructions.

2. The system of claim 1, wherein the assertion includes one or more keywords.

3. The system of claim 2, wherein the assertion further comprises a relationship between the one or more keywords.

4. The system of claim 1, wherein the imaging decision support system guides the text interpretation system.

5. A system for knowledge-based image computer aided detection comprising:
- a memory device storing a plurality of instructions embodying a knowledge-based image computer aided detection system;
- a processor for receiving an electronic patient record and executing the plurality of instructions to perform a method comprising:
  - determining and outputting an assertion relevant for the electronic patient record;
  - detecting anatomical and functional structures in an input image corresponding to the electronic patient record based on the assertion and outputting an annotated image; and
  - outputting a classification of an annotated structure in the annotated image based on the assertion; and
  - wherein the detecting anatomical and functional structures in input images is guided at least, in part by the assertion.

6. The system of claim 5, wherein the assertion includes one or more keywords.

7. The system of claim 6, wherein the assertion further comprises a relationship between the one or more keywords.

8. The system of claim 4, wherein the determining and outputting and assertion is guided by the imaging decision support system.

9. A computer readable medium embodying instructions executable by a processor to perform a method for knowledge-based image computer aided detection, the method comprising:
- receiving an electronic patient record;
- determining and outputting an assertion relevant for the electronic patient record;
- detecting anatomical and functional structures in an input image corresponding to the electronic patient record based on the assertion and outputting an annotated image; and
- outputting a classification an annotated structure in the annotated image based on the assertion; and
- wherein the detecting anatomical and functional structures in input images is guided at least in part by the assertion.

10. The method of claim 9, wherein the assertion includes one or more keywords.

11. The method of claim 10, wherein the assertion further comprises a relationship between the one or more keywords.

12. The method of claim 9, wherein the determining and outputting an assertion is guided by the imaging decision support system.

* * * * *